United States Patent
Schulz et al.

(10) Patent No.: US 6,605,425 B1
(45) Date of Patent: Aug. 12, 2003

(54) IMMUNOGENIC DETERMINANT FOR USE IN THE DIAGNOSIS OF KAPOSI'S SARCOMA

(76) Inventors: Thomas Friedrich Schulz, Heswall, Wirral LGO ODU (DE); Patrick S. Moore, 20 Quarry La., Irvington, NY (US) 10533; Guy R. Simpson, Surbiton, Surrey KT6 5PQ (GB); Yuan Chang, 20 Quarry La., Irvington, NY (US) 10533

( * ) Notice: Subject to any disclaimer, the term of this patent is extended or adjusted under 35 U.S.C. 154(b) by 0 days.

(21) Appl. No.: 09/254,592

(22) PCT Filed: Sep. 10, 1997

(86) PCT No.: PCT/GB97/02487
§ 371 (c)(1),
(2), (4) Date: Mar. 15, 2000

(87) PCT Pub. No.: WO98/11132
PCT Pub. Date: Mar. 19, 1998

(30) Foreign Application Priority Data

Sep. 10, 1996 (GB) .............................................. 9618890

(51) Int. Cl.[7] .......................... C12Q 1/70; G01N 33/53; C07K 7/00
(52) U.S. Cl. .......................... 435/5; 435/7.92; 530/300
(58) Field of Search ...................... 530/300; 424/184.1, 424/185.1, 186.1, 229.1, 207.1; 435/5, 7.1, 7.92

(56) References Cited

PUBLICATIONS

Merchant. Jan., 1996. An up–date on the herpesviruses. Journal of California Dental Association. vol. 24. No. 1, pp. 38–46. Abstract only.*

Dorland's Illustrated Medical Dictionary. 1994. 28th edition. W.B. Saunders Co., p. 1787.*

Chang et al. 1994. Identification of herpesvirus–like DNA sequences in AIDS–associated Kaposi's sarcoma. Science. vol. 266, pp. 1865–1869.*

Gao et al. Aug., 1996. KSHV antibodies among americans, italians, and ugandans with and without Kaposi's sarcoma. Nature Medicine. vol. 2, No. 8, pp. 925–928.*

Gao et al. Jul., 1996. Seroconversion to antibodies against Kaposi's sarcoma–associated herpesvirus–related latent nuclear antigens before the development of Kaposi's sarcoma. New England Journal of Medicine. vol. 335. No. 4, pp. 233–241.*

* cited by examiner

*Primary Examiner*—James Housel
*Assistant Examiner*—Shanon Foley
(74) *Attorney, Agent, or Firm*—Dykema Gossett PLLC

(57) ABSTRACT

The present invention relates to an immunogenic determinant. More particularly, it relates to a protein or a protein fragment for use in the diagnosis of Kaposi's sarcoma or human herpesvirus 8 (KSHV/HHV8) and to a diagnostic kit utilising the protein or protein fragment of the invention. The amino acid sequence of the carboxyterminal end of KSHV orf 65 is given below: Sequence 1: Amino acids 86–170 of KSHV orf 65. ADRVSAASY DAGTFTVPSR PGPASGTTPG GQDSLGVSGS SITTLSSGPH SLSPAS-DILT TLSSTTETTA PAVADARKPP SGKKK.

5 Claims, 2 Drawing Sheets

IMMUNOGENIC DETERMINANT FOR USE IN THE DIAGNOSIS OF KAPOSI'S SARCOMA

DESCRIPTION

The present invention relates to an immunogenic determinant. More particularly, it relates to a protein or a protein fragment for use in the diagnosis of Kaposi's sarcoma or human herpesvirus 8 (KSH/HHV8) and to a diagnostic kit utilising the protein or protein fragments of the invention.

Kaposi's sarcoma—relates herpesvirus (KSHV) or Human herpesvirus 8 (HHV 8) may be the postulated infectious cause of Kaposi's Sarcoma and is closely related to Epstein-Bar virus (HHV 5). Its prevalence in the general population is controversial. Antibodies to latent KSHV/HHV 8 antigen(s) are largely restricted to individuals with, and at risk for, KS. The antibody response to different EBV antigens (viral capsid, early, latent antigen) varies in individuals with acute, latent, or reactivated EBV infection.

Epidemiological evidence suggest that Kaposi's sarcoma in both HIV-uninfected and -infected individuals is caused by a transmissible agent: Among HIV-infected patients KS is much more common in gay men than in other HIV transmission groups, in particular haemophiliacs, transfusion recipients and intravenous drug users (IVDU). Transmission of the putative KS agent occurs independently of that of HIV and shows a marked geographic variation. Similarly, the incidence of KS outside HIV infection differs dramatically in different geographic areas: In Africa, it is higher in central and Eastern Africa than in West or South Africa, and in Europe, it is commoner in some Mediterranean countries.

The recently discovered Kaposi Sarcoma associated herpesvirus (KSHV), or human herpesvirus 8 (HHV8) is a $\gamma_2$-herpesvirus and closely related to EBV. KSHV/HHV 8 may be the infectious cause of KS, as it is consistently found in all forms of Kaposi's sarcoma, i.e. AIDS-related KS, African endemic KS, classic HIV-negative KS and KS in transplant patients. KSHV/HHV 8 genomes are present in endothelial and spindle cells, the histological hallmark of KS lesions. Detection of KSHV/HHV 8 in peripheral blood correlates with, and in asymptomatic HIV-infected individuals predicts the development of, KS lesions. However, whether the distribution of KSHV/HHV 8 matches that expected for the putative KS agent, is still controversial: while several groups have not detected KSHV/HHV 8 by PCR in the peripheral blood of healthy blood donors, others have reported its presence in 9% of PBMC and lymphoid tissue from HIV-uninfected persons. Similarly, some, but not other groups have reported a high prevalence in semen samples from healthy donors. More recently, the first serological studies have been carried out using immunoblotting and immunofluorescence assays on B-cell lymphoma cell lines, either dually infected with KSHV/HHV 8 and EBV, (Moore, P. S., Gaso, S. -J., Dominguez, G., et al. Primary characterization of a herpesvirus agent associated with Kaposi's sarcoma. J. Virol. 1996; 70: 549–558; Miller, G., Rigsby, M. O., Heston, L., et al. Antibodies to butyrate-inducible antigens of Kaposi's sarcoma—associated herpesvirus in patients with HIV-1 infection. N. Engl. J. Med. 1996; 334:1292–1297; Gao, S. J., Kingsley, L., Hoover, D. R. et al. Seroconversion of antibodies to Kaposi's sarcoma-associated herpesvirus—related latent nuclear antigens before the development of Kaposi's sarcoma. N. Engl. J. Med. 1996; 335: 233–241) or only infected with KSHV/HHV 8 (Gao, S. J. Kingsley, L., Li, M. et al. Seroprevalence of KSHV antibodies among North Americans, Italians, and Ugandans with and without Kaposi's sarcoma. Nature Medicine 1996; 2: 925–928 (Kedes, D. H., Operskalski, E., Busch, M. et al. The seroprevalence of human herpesvirus 8 (HHV 8): Distribution of infection in Kaposi's sarcoma risk groups and evidence for sexual transmission. Nature Medicine 1996; 2: in press). Antibodies to latent KSHV/HHV 8 antigen(s) were found in the vast majority of KS patients, but not, or only rarely, in HIV-infected IVDU, haemophiliacs, or healthy blood donors. Seroconversion to latent nuclear antigens can occur years prior to KS ones: and is strongly predictive of subsequent disease (Gao, S. J., Kingsley, L., Hoover, D. R. et al. Seroconversion of antibodies to Kaposi's sarcoma-associated herpesvirus-related latent nuclear antigens before the development of Kaposi's sarcoma. N. Engl. J. Med. 1996; 335: 233–241; Gao, S. J., Kinglsey, L., Li, M. et al. Seroprevalence of KSHV antibodies among North Americans, Italians, and Ugandans with and without Kaposi's sarcoma. Nature Medicine 1996; 2: 925–928). The antibody response to different antigen complexes (latent, capsid, early antigen) of the closely related EBV varies in acutely vs. chroncially infected individuals or immunosuppressed patients with reactivated EBV infection (Crawford, D. H. Epstein-Barr Virus in: Clinical Virology, Zuckerman, A. J., Banarvala, J. E., Pattison, J.R. eds., John Wiley & Sons, New York 1995; pp. 109–14; Horneff, M. W. Bein, G., Fricke, L., et al. Coincidence of Epstein-Barr virus reactivation, cytomegalovirus infection, and rejection episodes in renal transplant recipients. Transplantation 1995; 60: 474–480). Several potentially immunoreactive lytic-cycle proteins of KSHV/HHV 8, including the major capsid protein (MCP), are highly homologous to their EBV counterparts (Moore, P. S., Gao, S. -J., Dominguez, G., et al. Primary characterization of a herpesvirus agent associated with Kaposi's sarcoma J. Virol. 1996; 70: 549–558) and are thus unlikely to provide specific serological antigens.

In seeking an immunogenic determinant, recombinant proteins were generated in E. Coli from a number of orf encoded genes of KSHV/HHV8.

Particularly favourable results were obtained with a recombinant protein of orf 65—a lytic cycle/capsid related structural protein. This was particularly surprising given that KSHV/HHV8 homologues of at least two immunoreactive EBV proteins orf 52 and orf 29b had failed to react (as recombinant proteins) with sera from patients with Kaposi's Sarcoma.

More particularly the applicant has determined that the immunogenic region of the orf 65 protein was to be found at or within the carboxyterminal end—ie about the last 80 amino acids.

The amino acid sequence of the carboxyterminal end of KSHV orf 65 is given below:

Sequence 1: Amino acids 86–170 of KSHV orf 65

It is an aim of the present invention to identify proteins and/or protein fragments for use in the diagnosis of Kaposi's Sarcoma and associated herpesvirus (KSHV/HHV8).

It is a further aim to produce diagnostic kits, such as for example, an ELISA kit or competitive assay kit using these proteins and/or protein fragments.

It is a further aim to produce monoclonal or polyclonal antibodies to these proteins and/or protein fragments.

According to a first aspect of the present invention there is provided an immunogenic determinant comprising, consisting of or containing an amino acid sequence substantially homologous with the carboxyterminal end of an orf 65 protein.

According to a second aspect of the present invention there is provided an immunogenic determinant comprising, consisting of or containing an amino acid sequence:
[SEQ ID NO: 1]
ADRVSAASAY DAGTFTVPSR PGPASGTTFG GQD-SLGVSGS SITTLSSGPH SLSPASDILT TLSSTTETAA PAVADARKPP SGGKKK According to a third aspect of the present invention there is a method of screening for an infection with KSHV and/or HHV8 which method utilises an immunogenic determinant of the invention.

According to a fourth aspect of the present invention there is provided an immunogenic determinant derived from the carboxyterminal end of an orf 65 protein for use in a vaccine or as a diagnostic tool against KSHV or HHV8.

According to a fifth aspect of the present invention there is provided an immuno-assay kit comprising an immunogenic determinant of the invention.

Preferably the kit is in the form of an ELISA or competitive assay kit.

According to a further aspect of the present invention there is provided an antibody directed to an immunogenic determinant of the invention.

Preferably the antibody is a monoclonal antibody.

Figure 1:
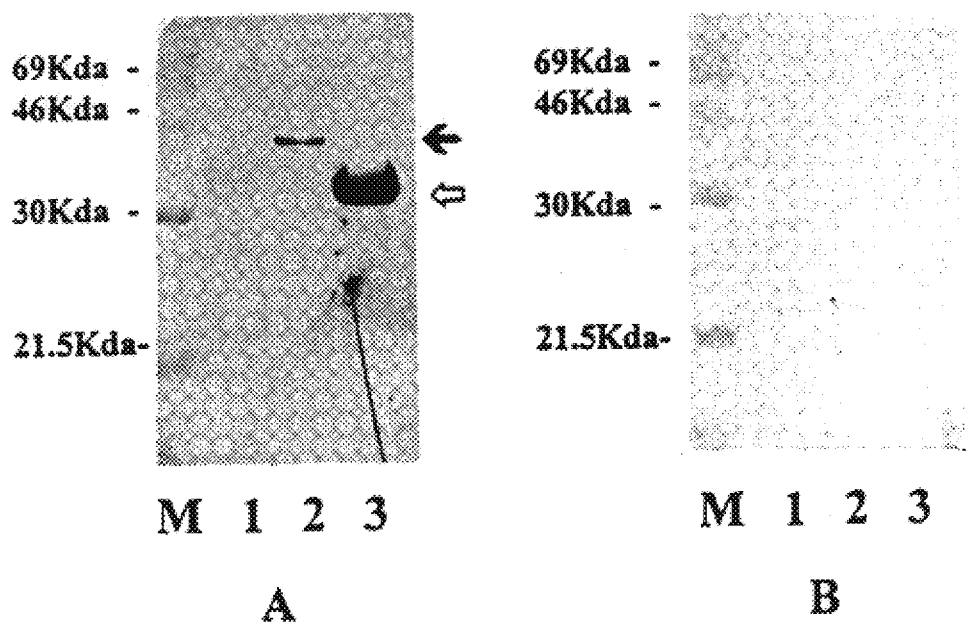
FIG. 1 shows a Western Blot with recombinant orf 65 and orf 52.
Figure 1:
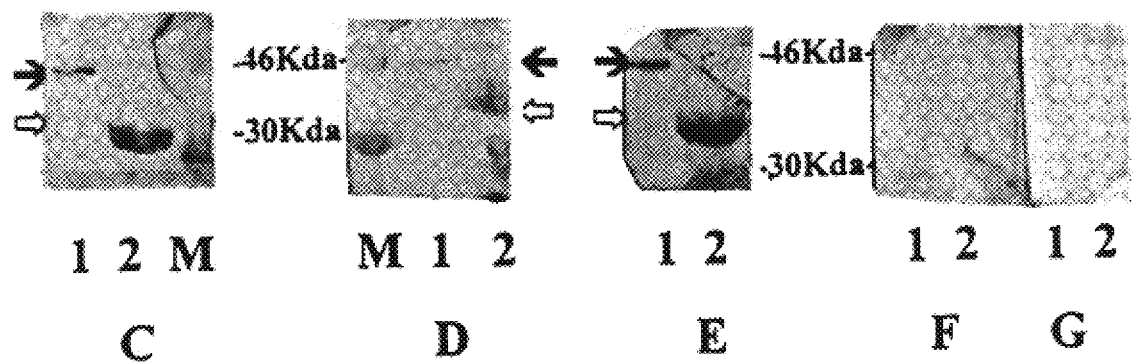

The invention will now be further described, by way of example only, with reference to the following methodology and test data.

Methods

Immunoreactive capsid-related proteins of KSHV/HHV 8 were selected by expressing them as recombinant proteins in *E. coli* and testing their reactivity with patient sera in Western blot assays. One of these recombinants, encoded by open reading frame (orf) 65 was used, to develop an immuno assay, namely a diagnostic ELISA and sera from HIV-infected individuals with KS, from classic HIV-uninfected KS patients, from other HIV risk groups and blood donors was tested. The antibody response to this capsid-related protein was compared to the response to HHV 8 latent antigen(s) as measured in an immunofluorescence assay (IFA).

Expression of recombinant HHV 8 proteins

Open reading frames (orf) 52 and 65 (or segments) were amplified by PCR, fused to the carboxyterminal end of mouse dihydrofolate reductase (DHFR), and placed under the control of a T7 promoter using a commercially available expression vector, pQE 42 (Qiagen, Hilden, Germany). This vector also provides a histidine tag at the aminoterminal end of the fusion protein.

To generate construct orf 65.1 (amino acids 2–170 or orf 65), the primers GAG AGA GAT CTG TTC CAA CTT TAA GGT GAG AGA C [SEQ ID NO: 2] and TCT GCA TGC CGG TTG TCC AAT CGT TGC CTA [SEQ ID NO: 3] were used. These primers generate a 589 bp fragment which was cloned using the BglII and SphI sites introduced during the PCR.

Construct orf 65.2 (amino acid 86–170) was assembled in a similar manner using primers AGA GAG ATC TGT GCT GAC CGA GTT TCC GCG GCG [SEQ ID NO: 4] and TCT GCA TGC CGG TTG TCC AAT CGT TGC CTA [SEQ ID NO: 5].

The orf 65.2 primers comprise respectively:
1) A stuffer sequence AGAG, a BglII restriction site AGATCT, GT and the coding sequence for the amino acids ADRVSAA [SEQ ID NO: 6], and
2) A stuffer sequence TCT, a SphI restriction site GCATGC, and a sequence CGG TTG TTC AAT CGT TGC [SEQ ID NO: 7] upstream of the CTA stop codon (amino acid number 171).

The carboxyterminal region of orf 65 (aa 86–170) is slightly less homologous (21% aa identity) to the equivalent region in EBV BFRF3 than the aminoterminal half (31% identity).

Recombinant proteins were purified by affinity chromatography on Ni-NTA resin as described by the manufacturer (Qiagen, Hilden, Germany).

ELISA with orf 65.2 protein

ELISA plates (Immulon 4; Dynatech) were coated with 100 µl of purified orf 65.2 protein (approximately 5 µg/ml) in 0.1 M NaHCO$_3$, pH 8.5 for 16 h at room temperature. A conventional ELISA protocol was employed using PBS, 0.1% Tween 20 (PBS-T) for washes, 5% dried skimmed milk in PBS-T (blocking buffer) to saturate plates and to dilute patient sera (1:100), and an alkaline phosphatase (AP) conjugated affinity-purified goat anti-human IgG (Seralab), diluted 1:1000 in blocking containing 1% goat serum, followed by 0.1 mg/ml of nitrophenyl phosphate (Sigma, St. Louis, USA) in glycine buffer (0.1 M glycine, 1 mM MgCl$_2$, 1 mM ZnCl, pH 10.4) as substrate. The colorimetric reaction was stopped after 1 hour at 37° C. with 50 µl of 3 M Na-hydroxide and read spectrophotometrically at 405 nm.

Immunofluoresence assay (IFA) for HHV 8 Antibodies

This was carried out on a body-cavity related B-cell lymphoma cell line latently infected with HHV 8 (BCP-1), as described in (Gao, S. J., Kinglsely, L., Li, M. et al. Seroprevalence of KSHV antibodies among North Americans, Italians, and Ugandans with and without Kaposi's sarcoma. *Nature Medicine* 1996; 2: 924–928). This assay detects antibodies to latent antigen(s) of HHV 8.

Patient sera

The following sera was analysed:
  78 sera from HIV infected gay men attending an HIV clinic, of whom 57 had KS and 21 had AIDS in the absence of KS;
  10 sera from HIV-infected Ugandan KS patients and 10 sera from Ugandan HIV-infected individuals without KS;
  18 sera from classic Greek KS patients and 26 sera from their age and sex matched controls, obtained from an ongoing case control study in Athens, Greece (A.H.);
  84 sera from haemophiliac patients, of whom 28 were infected with HIV;
  63 sera from intravenous drug users in Edinburgh, of whom 38 were infected with HIV; 174 sera from UK blood donors; and
  20 sera from US blood donors.

Statistical analysis

The concordance between IFA and ELISA was evaluated by calculating a κ statistic as described in (Fleiss, J. L. Statistical Methods for Rates and Proportions, 1981; 2nd edition).

Results

Selection of orfs and expression of recombinant antigens

FIG. 1 shows a Western Blot with recombinant orf 65 and orf 52, where 1=orf 52
  2=compete orf 65
  3=orf 65 aa 86–170

A=AIDS KS serum

B=blood donor system

C=UK AIDS KS serum (orf 65 ELISA+/IFA=/orf 65 WB+)

D=UK blood donor (orf 65 ELISA+/IFA−/orf 65 WB+)

E=Greek control patient (orf 65 ELISA+/IFA−/orf 65 WB+)

F=high tire EBV VCA serum (orf 65 ELISA+/orf 65 WB+)

G=UK blood donor (orf 65 ELISA+/IFA−/WB−)

Referring to FIG. 1 it will be seen that whilst both recombinant orf 65 proteins reacted well with most sera from KS patients (panel A, lanes 2,3), the recombinant orf 52 protein showed no significant reactivity (panel A, lane 1). Both recombinant orf 65.1 and orf 65.2 reacted with the same number of patient sera on Western blots. The carboxy-terminal regions of orf 65 and BFRF3 share only 18 evenly distributed amino acids (21% identity) which makes antibody cross-reactivity between them unlikely.

ELISA with recombinant orf 65

In the light of the aforementioned results the recombinant orf 65.2 was used as an antigen in a diagnostic ELISA.

Figure 2:
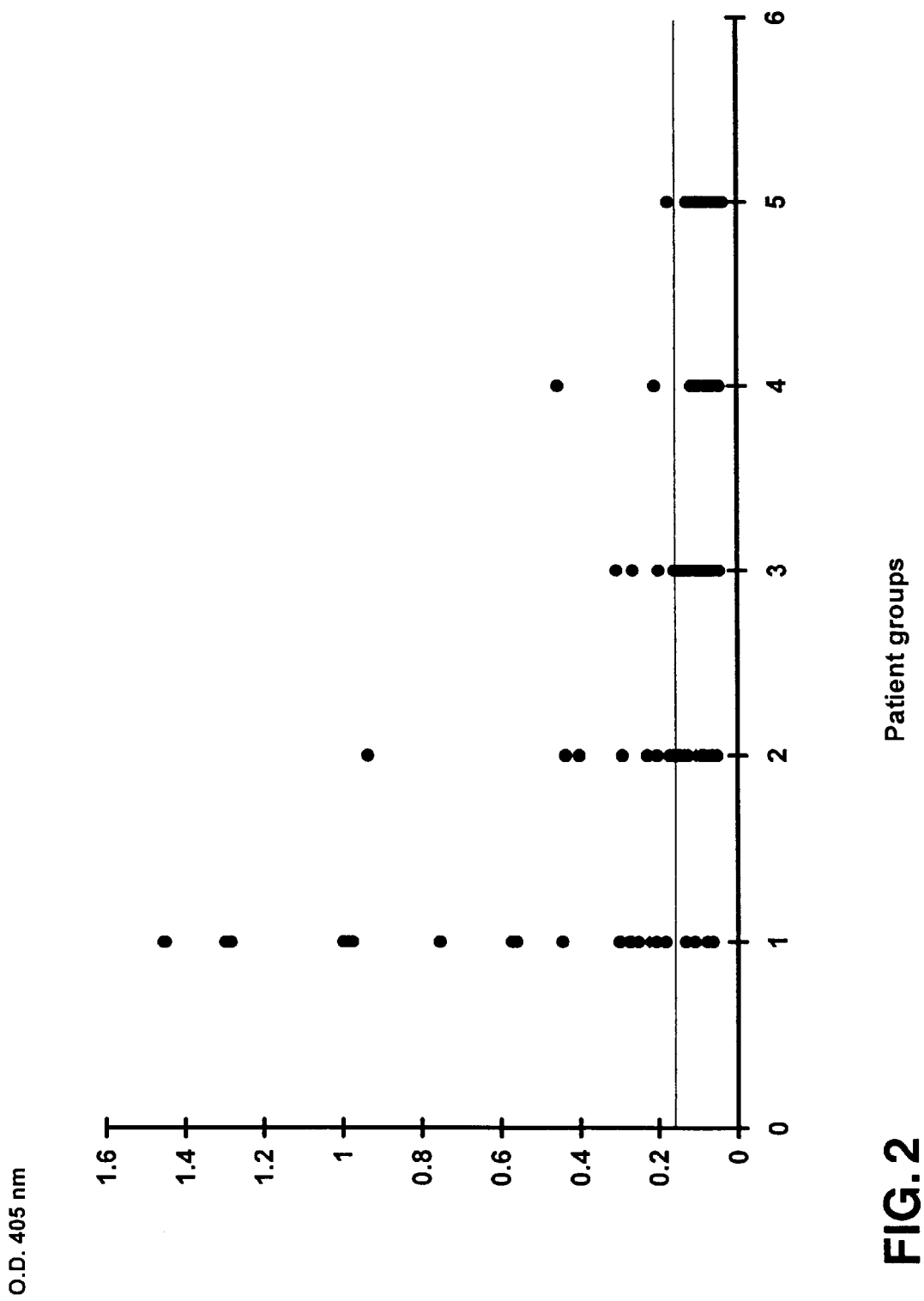
FIG. 2 shows an example of the ELISA results obtained with recombinant orf 654 protein on a selection of human sera.

FIG. 2 shows an example of the ELISA results obtained with recombinant orf 65 protein on a selection of human sera.

The results of 21 serum samples from the patient groups 1 to 5 were tested by ELISA at a 1:100 dilution. Patient groups 1 to 5 are as follows:

1: individuals with AIDS-associated KS;

2: AIDS patients without KS;

3: UK blood donors;

4: intravenous drug users;

5: haemophiliacs.

The thin line represents the "cut-off" value (0.16) determined as discussed in the text.

Among the AID-related KS patients many reactive samples were detected whilst among haemophiliacs, intravenous drug users (IVDU), and healthy blood donors only a few reactive samples were detected. To distinguish between reactive and unreactive sera, the mean of O.D. values of healthy blood donor sera (with the exception of the three strongly reactive sera shown in FIG. 2) plus three standard deviations as the "cut-off" value was used. To test blinded sera, the mean plus five standard deviations of a set of 10 negative controls to determine the "cut-off" value was used, and also include 2 sera which gave reactivities close to the cut-off, 2 low positive and 1 high positive sera, to ensure inter-assay comparability.

Using these criteria antibodies to orf 65 in 46 of 57 (80.7%) UK or US AIDS-KS sera, 8 of 10 (80.0%) Ugandan AIDS-KS sera, and 17 out of 18 (94.4%) of HIV-negative classic KS sera were detected as shown in Table 1 below:

TABLE 1

Antibodies to orf 65 protein of KSHV/HHV 8 in different HIV risk groups and controls

| Risk groups | positive/tested | % positive |
| --- | --- | --- |
| AIDS-KS | | |
| UK/US | 46/57 | 80.7 |
| Uganda | 8/10 | 80.0 |
| Classic Greek KS | 17/18 | 94.4 |

TABLE 1-continued

Antibodies to orf 65 protein of KSHV/HHV 8 in different HIV risk groups and controls

| Risk groups | positive/tested | % positive |
| --- | --- | --- |
| HIV-infected gay men | | |
| without KS | 5/16 | 31.3 |
| Haemophiliacs | 1/84 | 1.2 |
| HIV infected | 0/28 | 0.0 |
| HIV uninfected | 1/56 | 1.7 |
| IVDU | 2/63 | 3.2 |
| HIV infected | 2/38 | 5.3 |
| HIV uninfected | 0/25 | 0.0 |
| Blood donors* | | |
| UK | 3/174 | 1.7 |
| USA | 1/20 | 5.0 |
| Greek age/sex matched controls** | 3/26 | 11.5 |
| Ugandan controls | 7/10 | 70.0 |

*Confirmed by Western blot on recombinant orf 65.1 and orf 65.2 (FIG. 1). 11 blood donor sera were initially reactive in die orf 65.2 ELISA
**confirmed by Western blot or IFA Among gay men with AIDS, but no KS, antibodies in 5 of 16 cases were detected (31.3%) $18/18$ ELISA—reactive sera from individuals with AIDS-KS or AIDS in the absence of KS were also reactive by Western blot on recombinant orf 65.1 and 65.2 antigen (FIG. 1).

In contrast, antibodies to orf 65 were only detected infrequently in other risk groups for HIV transmission: $1/84$ haemophiliac patients (1.2%) and $2/63$ intravenous drug users (IVDU) (3.2%) had antibodies to HHV 8 orf 65 (Table 1). Among UK blood donors, $11/169$ sera were reactive by ELISA. Of these, 3 sera were confirmed as positive by Western blotting using both recombinant orf 65.1 and orf 65.2 antigens (FIG. 1), suggesting a prevalence of KSHV/HHV 8 infection in UK blood donors of at least 1.6% Table 1). 3 of 26 Greek control sera were reactive by ELISA obtained from individuals who had been matched to the 18 classical KS cases by age an sex (Table 1). All 3 ELISA reactive Greek control sera were also positive by WB and/or IFA, amounting to a seroprevalence of KSHV/HHV 8 in Greek elderly individuals of 11.5%. In contrast, infection with KSHV/HHV 8 seems to be more widespread in Uganda, as $7/10$ (70%) control samples had antibodies to KSHV/HHV 8 orf 65. Blinded sequential sera from 14 KS patients (2–4 sera from each individual) were also tested and concordant results were obtained. Only one individual was obtained in whose last (of three) serum sample antibodies were no longer detected to the orf 65 encoded protein.

Concordance of KSHV/HHV 8 antibody detection by orf 65 ELISA and immunofluorescence The detection of antibodies to orf 65 and to latent KSHV/HHV8 antigens was compared by testing sera fro KS patents, individuals at risk for KS (gay men with AIDS, but without KS; Ugandan HIV-infected individuals), and UK and US blood donors in the orf 65 ELISA and immunofluorescence (IFA) on BCP-1 cells. There results are shown in table 2 below:

TABLE 2

Comparison of antibody reactivity to orf 65 protein and to latent antigen(s)

Reactivity to KSHV/HHV 8 latent antigen (IFA)

|  | KS* | | HIV-infection: no KS** | | UK/US blood donors*** and Greek controls | |
| --- | --- | --- | --- | --- | --- | --- |
|  | + | − | + | − | + | − |
| Reactivity to + KSHV/HHV 8 orf 65 − (ELISA/WB) | 62 | 7 | 7 | 5 | 2 | 4 |
|  | 9 | 4 | 3 | 11 | 5 | 196 |
|  | $\kappa = 0.21$ $p = 0.023$ (1-tailed) | | $\kappa = 0.37$ $p = 0.026$ (1-tailed) | | $\kappa = 0.29$ $p = 0.000019$ (1-tailed) | |

*includes UK/US and Ugandan AIDS KS cases
**includes HIV-infected gay men with AIDS, but without KS, and HIV-infected Ugandan subjects without KS
***includes Western blot confirmed blood donor results as discussed in the text.

There was good agreement between the two assays. 89.5% of all sera (282/315) showed a concordant result. 71 of 88 (80.7%) IF-positive sera were also positive by ELISA and 71 of 87 (81.6%) ELISA positive sera were also reactive in immunofluorescence. Among the 14 AIDS—related KS patients from whom sequential sera were available, 3 individuals who consistently lacked antibodies to the orf 65—encoded protein despite being (on at least one occasion) reactive by IFA were observed, suggesting that the lack of orf 65 reactivity can be a stable phenomenon. 4 individuals were also observed with AIDS-related KS who were negative in both assays. The 3 ELISA-reactive, WB-confirmed UK blood donor sera were negative by IFA. Among the Ugandan samples tested, the concordance rate was 14/20 (70.0%) with 12/15 IFA-reactive samples being also ELISA reactive (80.0%), and 12/15 ELISA-reactive samples being also positive in IFA (80.0%). This suggests that the high rate of KSHV/HHV 8 infection among HIV-infected Ugandans found by ELISA is genuine, and not due to non-specific reactivity.

Findings

The KSHV/HHV 8 orf 65 protein is recognised by the majority of sera from KS patients and its dominant immunogenic region is located within the carboxyterminal amino acids. This region shows only little homology (21% amino acid identity) with the corresponding region in the EBV genome and is thus likely to represent a specific serological antigen. By ELISA, the applicants detected antibodies to this domain in 46 of 57 (80.7%) UK AIDS-KS era sera, 8 of 10 (80.0%) Ugandan AIDS-KS sera, 17 out of 18 (94.4%) of HIV-negative classic KS sera, 1 out of 84 (1.2%) of haemophiliac sera, and 2 of 63 (3.2%) of IV drug user sera. 3 (of 174; 1.7%) ELISA reactive UK blood donor sera were confirmed by Western blot (WB) on recombinant proteins. Antibody reactivity to the orf 65 encoded protein and to latent antigen(s), measured by immunofluorescence, was concordant in 89.5% of all sera tested in both assays. A few sera; including four AIDS-KS sera, were unreactive in both assays. The three ELISA- and WB-positive blood donor sera were unreactive with latent KSHV/HHV 8 antigen(s) in immunofluorescence.

Interpretation

The distribution of antibodies to both a capsid-related recombinant protein and latent antigen(s) of KSHV/HHV 8 strongly support the view that infection with this virus is largely confined to individuals with, or at increased risk for, KS. However, infection with KSHV/HHV 8 does occur rarely in the general UK and US population and is more common in Uganda. Measured on their own, antibodies to neither latent antigen(s), nor to the orf 65 encoded capsid protein, detect all cases of KSHV/HHV 8 infection, and a combination of these antigens will be preferred for accurate screening assays. The results demonstrate the recombinant HHV 8 protein is recognised by the majority of sera from KS patients and is therefore useful for the serological diagnosis of infection with KSHV/HHV 8.

Orf 65 encodes a protein which, based on its positional and (low) sequence homology with EBV BFRF3 is likely to be a capsid protein and is therefore expressed during the lytic cycle of viral replication. Because of its predicted low molecular weight (about 18 kd) it is not identical with a previously described 40 kd lytic-cycle HHV 8 protein, recognised by about 67% of patient sera, or the 27 kd and 60 kd lytic-cycle proteins which react with only a small proportion of KS sera. As in the case of EBV BFRF3, the immunogenic determinants in the orf 65-encoded protein are located in its carboxyterminal half which shares only 21% of its amino acids with the corresponding BFRF3 segment. This region (aa 86–170) is therefore a good candidate for a specific serological antigen. Latently infected body-cavity related B-cell lymphoma cell lines (BCBL) express at least one latent antigen which has been reported to react (in IFA) with about 90% of sera from AIDS-related KS patients and whose identity is presently unknown. A high molecular weight immunoreactive doublet antigen which is localised to the nucleus has also been reported but it is unknown whether this is the antigen being assayed in the BCP −1 IFA assay.

Using an ELISA based on recombinant orf 65.2 protein (aa 86–170 of orf 65), the applicant has found that 80.7% of AIDS-KS sera, and 94.4% of HIV-negative 'classical' KS sera, contain antibodies to this HHV 8 protein. In contrast, antibodies to orf 65 are only rarely found in haemophiliacs and IV drug users who have a low risk of developing KS, even after infection with HIV. Thus antibodies to both latent and capsid protein of KSHV/HHV 8 are rare in individuals at low risk for KS. In analogy to EBV, where antibodies to VCA (viral capsid antigen) and EBNA (EBV latent antigen) persist after infection with EBV, it is thus likely that the antibody response to both latent and capsid proteins of KSHV/HHV 8 is due to infection with, rather than reactivation of, KSHV/HHV 8. Thus serological data support the conclusion, that infection with HHV 8 is not common in the general UK and US population. It was found that the sensitivity of both the orf 65 ELISA and IFA were comparable and that a similar number of sera was missed by either assay alone. The applicant detected 3 (of 174; 1.6%) UK blood donor sera with Western blot confirmed antibody reactivity to orf 65 which scored negative in the immunofluorescence assay. In view of the low homology between orf 65 and EBV BFRF3 it is very unlikely that these sera could have contained antibodies to EBV BFRF3 which cross-reacted with the orf 65.2 recombinant protein. Of 10 sera with high titre EBV VCA antibodies none reacted with both recombinant orf 65 proteins. However, taken together with the recently reported small number of IFA-reactive US blood donor sera. (, these findings suggest a low percentage of KSHV/HHV 8—infected individuals in the general UK and US populations. The results with capsid-related antigen also confirm that KSHV/HHV 8 infection is more common in some parts of Africa (e.g. Uganda) than in the UK or US but its exact prevalence in different geographical areas remains to be established, most likely by a combination of tests measuring antibodies to both lytic and latent antigens, as illustrated here.

What is claimed is:

1. An isolated immunogenic protein fragment consisting essentially of amino acids having the amino acid sequence ADRVSAASAY DAGTFTVPSR PGPASGTTPG GQDSLGVSGS SITTLSSGPH SLSPASDILT TLSSTTETTA PAVADARKPP SGKKK (Sequence Id. No. 1).

2. An immunoassay kit which comprises the immunogenic protein fragment of claim 1 and one or more reagents adapted for use with the immunogenic protein fragment of claim 1 to screen for a KSHV and/or HHV8 infection.

3. The immunoassay kit of claim 2, wherein the immunoassay kit is an ELISA immunoassay kit, the kit including reagents adapted for use with the immunogenic protein fragment of claim 1 to screen for a KSHV and/or HHV8 infection.

4. The immunoassay kit of claim 2, the kit including reagents adapted for use with the immunogenic protein fragment of claim 1 to screen for a KSHV and/or HHV8 infection.

5. A method of screening for a KSHV and/or HHV8 infection, which comprises:

providing the isolated immunogenic protein fragment of claim 1;

reacting said serum sample and said protein fragment in a suitable substrate; and characterizing the reactivity.

* * * * *

UNITED STATES PATENT AND TRADEMARK OFFICE
CERTIFICATE OF CORRECTION

PATENT NO. : 6,605,425 B1  
DATED : August 12, 2003  
INVENTOR(S) : Schulz et al.

It is certified that error appears in the above-identified patent and that said Letters Patent is hereby corrected as shown below:

Column 11,  
Line 26, Sequence ID No. 1 should read as follows:  
-- ADRVSAASAY DAGTFTVPSR PGPASGTTPG GQDSLGVSGS SITTLSSGPH SLSPASDILT TLSSTTETAA PAVADARKPP SGKKK --

Signed and Sealed this

Twenty-third Day of December, 2003

JAMES E. ROGAN  
*Director of the United States Patent and Trademark Office*

SEQUENCE LISTING

<160> NUMBER OF SEQ ID NOS: 7

<210> SEQ ID NO 1
<211> LENGTH: 85
<212> TYPE: PRT
<213> ORGANISM: KSHV

<400> SEQUENCE: 1

Ala Asp Arg Val Ser Ala Ala Ser Ala Tyr Asp Ala Gly Thr Phe Thr
1               5                   10                  15

Val Pro Ser Arg Pro Gly Pro Ala Ser Gly Thr Thr Pro Gly Gly Gln
            20                  25                  30

Ala Ser Leu Phe Val Ser Gly Ser Ser Ile Thr Thr Leu Ser Ser Gly
        35                  40                  45

Pro His Ser Leu Ser Pro Ala Ser Asp Ile Leu Thr Thr Leu Ser Ser
    50                  55                  60

Thr Thr Glu Thr Ala Ala Pro Ala Val Ala Asp Ala Arg Lys Pro Pro
65                  70                  75                  80

Ser Gly Lys Lys Lys
            85

<210> SEQ ID NO 2
<211> LENGTH: 33
<212> TYPE: DNA
<213> ORGANISM: Unknown
<220> FEATURE:
<223> OTHER INFORMATION: primer

<400> SEQUENCE: 2
gagagagatc tgttccaact ttaaggtgag aga                        33

<210> SEQ ID NO 3
<211> LENGTH: 30
<212> TYPE: DNA
<213> ORGANISM: Unknown
<220> FEATURE:
<223> OTHER INFORMATION: primer

<400> SEQUENCE: 3
tctgcatgcc ggttgtccaa tcgttgccta                           30

<210> SEQ ID NO 4
<211> LENGTH: 33
<212> TYPE: DNA
<213> ORGANISM: Unknown
<220> FEATURE:
<223> OTHER INFORMATION: primer

<400> SEQUENCE: 4
agagagatct gtgctgaccg agtttccgcg gcg                        33

<210> SEQ ID NO 5
<211> LENGTH: 30
<212> TYPE: DNA
<213> ORGANISM: Unknown
<220> FEATURE:
<223> OTHER INFORMATION: primer

<400> SEQUENCE: 5
tctgcatgcc ggttgtccaa tcgttgccta                           30

```
<210> SEQ ID NO 6
<211> LENGTH: 7
<212> TYPE: PRT
<213> ORGANISM: KSHV

<400> SEQUENCE: 6

Ala Asp Arg Val Ser Ala Ala
1               5

<210> SEQ ID NO 7
<211> LENGTH: 18
<212> TYPE: DNA
<213> ORGANISM: Unknown
<220> FEATURE:
<223> OTHER INFORMATION: primer

<400> SEQUENCE: 7
cggttgttca atcgttgc                                                   18
```